(12) United States Patent
Olson et al.

(10) Patent No.: US 11,795,495 B1
(45) Date of Patent: Oct. 24, 2023

(54) MACHINE LEARNED EPIGENETIC STATUS ESTIMATOR

(71) Applicant: Life Epigenetics, Inc., Minneapolis, MN (US)

(72) Inventors: Randal S. Olson, Minneapolis, MN (US); Brian H. Chen, Minneapolis, MN (US)

(73) Assignee: FOXO Labs Inc., Minneapolis, MN (US)

( * ) Notice: Subject to any disclaimer, the term of this patent is extended or adjusted under 35 U.S.C. 154(b) by 780 days.

(21) Appl. No.: 16/591,296

(22) Filed: Oct. 2, 2019

(51) Int. Cl.
| | | |
|---|---|---|
| *C12Q 1/6825* | (2018.01) | |
| *G16H 10/60* | (2018.01) | |
| *G16H 50/50* | (2018.01) | |
| *G16B 5/20* | (2019.01) | |
| *G16H 50/20* | (2018.01) | |
| *G16H 50/70* | (2018.01) | |
| *G16B 40/10* | (2019.01) | |
| *G16H 50/30* | (2018.01) | |
| *G01N 33/53* | (2006.01) | |
| *G16B 20/00* | (2019.01) | |
| *G16B 40/30* | (2019.01) | |
| *G16B 40/00* | (2019.01) | |
| *C12Q 1/6869* | (2018.01) | |

(Continued)

(52) U.S. Cl.
CPC ......... *C12Q 1/6825* (2013.01); *C12Q 1/6869* (2013.01); *C12Q 1/6876* (2013.01); *G01N 33/53* (2013.01); *G16B 5/20* (2019.02); *G16B 20/00* (2019.02); *G16B 40/00* (2019.02); *G16B 40/10* (2019.02); *G16B 40/20* (2019.02); *G16B 40/30* (2019.02); *G16H 10/60* (2018.01); *G16H 50/20* (2018.01); *G16H 50/30* (2018.01); *G16H 50/50* (2018.01); *G16H 50/70* (2018.01)

(58) Field of Classification Search
CPC ........ G16H 10/00–80/00; G06N 3/00–99/007; C12Q 1/00–2600/178; G16B 5/00–99/00
See application file for complete search history.

(56) References Cited

U.S. PATENT DOCUMENTS

| | | | |
|---|---|---|---|
| 6,566,061 | B1 | 5/2003 | Philibert et al. |
| 8,637,652 | B2 | 1/2014 | Philibert et al. |

(Continued)

FOREIGN PATENT DOCUMENTS

| | | | | |
|---|---|---|---|---|
| WO | WO-2011032040 | A1 * | 3/2011 | ........... C12Q 1/6827 |
| WO | WO-2011036604 | A2 * | 3/2011 | ........... C12Q 1/6813 |

(Continued)

OTHER PUBLICATIONS

Matsuzaki et al., "Decision making model supporting emergency medical care," 2009 International Conference on Biometrics and Kansei Engineering, 2009 IEEE Computer Society. (Year: 2009).*

(Continued)

*Primary Examiner* — Jonathon A. Szumny
(74) *Attorney, Agent, or Firm* — Lee & Hayes, P.C.

(57) ABSTRACT

A machine learning (ML) architecture may be trained to determine an estimated epigenetic status at a target DNA locus based at least in part on epigenetic data associated with one or more other DNA loci. The ML architecture may additionally or alternatively be used to detect a failed epigenetic assay and/or determine a likelihood that a subject has falsified information provided about the subject.

20 Claims, 6 Drawing Sheets

(51) Int. Cl.
*G16B 40/20* (2019.01)
*C12Q 1/6876* (2018.01)

(56) References Cited

U.S. PATENT DOCUMENTS

| | | | |
|---|---|---|---|
| 9,273,358 B2 | 3/2016 | Philibert et al. | |
| 9,994,904 B2 | 6/2018 | Philibert et al. | |
| 11,322,224 B2* | 5/2022 | Rabinowitz | C12Q 1/6862 |
| 11,445,981 B1* | 9/2022 | Fortney | G16H 20/10 |
| 2002/0192686 A1* | 12/2002 | Adorjan | C12Q 1/6883 |
| | | | 435/6.12 |
| 2003/0190602 A1* | 10/2003 | Pressman | C12Q 1/6809 |
| | | | 435/5 |
| 2004/0038254 A1* | 2/2004 | Peoples | C12Q 1/6827 |
| | | | 435/6.12 |
| 2004/0132037 A1* | 7/2004 | Prasanna | G01N 33/6875 |
| | | | 435/6.12 |
| 2004/0210400 A1* | 10/2004 | Konvicka | G16B 20/40 |
| | | | 702/20 |
| 2005/0272070 A1* | 12/2005 | Ehrich | C12Q 1/6848 |
| | | | 435/6.12 |
| 2007/0248576 A1 | 10/2007 | Philibert et al. | |
| 2007/0292880 A1 | 12/2007 | Philibert et al. | |
| 2009/0094065 A1 | 4/2009 | Hyde et al. | |
| 2011/0223180 A1 | 9/2011 | Aldape et al. | |
| 2011/0318735 A1 | 12/2011 | Philibert et al. | |
| 2012/0108444 A1 | 5/2012 | Philibert et al. | |
| 2012/0157322 A1* | 6/2012 | Myllykangas | C12Q 1/6806 |
| | | | 435/91.2 |
| 2012/0157324 A1 | 6/2012 | Lizardi et al. | |
| 2012/0164238 A1* | 6/2012 | Joost | A61P 35/00 |
| | | | 435/6.12 |
| 2013/0288247 A1* | 10/2013 | Mori | C12Q 1/6886 |
| | | | 435/6.11 |
| 2014/0143188 A1 | 5/2014 | Mackey et al. | |
| 2014/0279754 A1* | 9/2014 | Barsoum | G06N 7/005 |
| | | | 706/12 |
| 2015/0066824 A1* | 3/2015 | Harris | C12Q 1/6869 |
| | | | 706/13 |
| 2015/0193577 A1 | 7/2015 | Xiang et al. | |
| 2016/0210403 A1* | 7/2016 | Zhang | G16B 40/20 |
| 2016/0340731 A1* | 11/2016 | Cookson | C12Q 1/6883 |
| 2017/0132362 A1 | 5/2017 | Skinner et al. | |
| 2017/0183728 A1 | 6/2017 | Philibert et al. | |
| 2017/0306405 A1 | 10/2017 | Philibert | |
| 2017/0306408 A1 | 10/2017 | Philibert et al. | |
| 2018/0065248 A1* | 3/2018 | Barral | G06N 20/00 |
| 2018/0150713 A1* | 5/2018 | Farooqi | G06K 9/6268 |
| 2018/0216195 A1* | 8/2018 | Elnitski | C12Q 1/6886 |
| 2018/0315494 A1* | 11/2018 | Kolde | G16H 10/60 |
| 2019/0264286 A1* | 8/2019 | Dogan | C12Q 1/6883 |
| 2020/0056245 A1* | 2/2020 | Lo | C12Q 1/6869 |
| 2021/0017587 A1* | 1/2021 | Cai | C12Q 1/6841 |
| 2021/0073618 A1* | 3/2021 | Boussarov | G06N 3/08 |
| 2021/0155695 A1* | 5/2021 | Chinnaiyan | A61K 39/39558 |
| 2021/0388445 A1* | 12/2021 | Gore | C12Q 1/6886 |
| 2022/0076779 A1* | 3/2022 | Feinberg | G16B 40/00 |

FOREIGN PATENT DOCUMENTS

| | | | | |
|---|---|---|---|---|
| WO | WO-2013041731 A1 * | 3/2013 | | C12Q 1/6886 |
| WO | WO-2014165267 A2 * | 10/2014 | | C12Q 1/6827 |
| WO | WO-2016029088 A1 * | 2/2016 | | C07H 21/04 |
| WO | WO-2016109284 A1 * | 7/2016 | | A61K 31/7068 |
| WO | WO-2017046714 A1 * | 3/2017 | | |
| WO | WO2017214397 A1 | 12/2017 | | |
| WO | WO-2017218908 A2 * | 12/2017 | | G16B 20/00 |
| WO | WO2018027228 A1 | 2/2018 | | |
| WO | WO-2019195941 A1 * | 10/2019 | | |

OTHER PUBLICATIONS

Feng et al., "Disease prediction by cell-free DNA methylation," Briefings in Bioinformatics, 20(2), 2019, 585-597, doi: 10.1093/bib/bby029. (Year: 2019).*

Lussier et al., "DNA methylation as a predictor of fetal alcohol spectrum disorder," Clinical Epigenetics (2018) 10:5 DOI 10.1186/s13148-018-0439-6. (Year: 2018).*

Vidaki et al., "DNA methylation-based forensic age prediction using artificial neural networks and next generation sequencing," Forensic Science International: Genetics 28 (2017) 225-236. (Year: 2017).*

Tian et al., "MRCNN: a deep learning model for regression of genome-wide DNA methylation," BMC Genomics 2019, 20(Suppl 2): 192 https://doi.org/10.1186/s12864-019-5488-5. (Year: 2019).*

Ayush Alag, "Machine learning approach yields epigenetic biomarkers of food allergy: A novel 13-gene signature to diagnose clinical reactivity," Plos One 14(6): e0218253. https://doi.org/10.1371/journal.pone.0218253. (Year: 2019).*

Levy-Jurgenson et al., "Predicting Methylation from Sequence and Gene Expression Using Deep Learning with Attention," bioRxiv preprint doi: https://doi.org/10.1101/491357; posted Dec. 9, 2018 (Year: 2018).*

Dong et al., "Predicting overall survival of patients with hepatocellular carcinoma using a three-category method based on DNA methylation and machine learning," J Cell Mol Med. 2019;23:3369-3374, DOI: 10.1111/jcmm.14231. (Year: 2019).*

Paez et al., "Genome coverage and sequence ®delity of f29 polymerase-based multiple strand displacement whole genome amplification," Nucleic Acids Research, 2004, vol. 32, No. 9 e71 DOI: 10.1093/nar/gnh06. (Year: 2004).*

* cited by examiner

MACHINE LEARNED EPIGENETIC STATUS ESTIMATOR

BACKGROUND

A variety of assays exist to detect epigenetic levels at a DNA segment, such as bisulfite sequencing, pyrosequencing, microarrays, and/or the like. Some methods, such as bisulfite sequencing may be used to detect DNA methylation levels across an entire genome and other methods, such as microarrays configured with particular sets of probes, may test one or more loci within a genome for methylation—for example, a particular probe on the microarray may detect a methylation level at a locus in the DNA (e.g., a locus may be associated with one or more base pairs).

However, in some instances, detecting the methylation level at a DNA locus may be inaccurate, completely fail, or otherwise be unavailable. For example, a primer for bisulfite sequencing may be methylated and may confound the methylation level detected at a DNA locus, DNA quality may degrade, a probe on a microarray may fail, inconsistent DNA conversion methods, a microarray may not include a probe for testing a particular DNA locus, a scanner for detecting radiation or luminescence may misread a probe, and/or the like. Moreover, in some instances, a probe failure or inaccurate methylation level may be difficult or impossible to detect because of the sheer number of DNA loci tested for methylation.

BRIEF DESCRIPTION OF THE DRAWINGS

The detailed description is described with reference to the accompanying figures. In the figures, the left-most digit(s) of a reference number identify the figure in which the reference number first appears. The same reference numbers in different figures indicate similar or identical items.

DETAILED DESCRIPTION

The techniques (e.g., process(es) and/or machine(s)) discussed herein generally relate to training a machine learning (ML) architecture for determining an estimated epigenetic level at a target DNA locus. As used herein, a DNA locus may comprise any one or more base pairs of a DNA sequence. For example, a DNA locus may include a particular position in the chromosome, an individual base pair, and/or a particular sequence of nucleic acids, such as a CpG island. Epigenetic data may comprise a measurement of methylation, acetylation, histone, and/or other similar modifications to DNA, RNA, or proteins. In some examples, the epigenetic data may be acquired from a biological sample received from the subject. The biological sample may comprise saliva and/or blood, although it is contemplated that other samples may be collected from the subject.

The ML model discussed herein may be trained to receive one or more epigenetic values associated, respectively, with one or more DNA loci and to estimate an epigenetic level of a target DNA locus based on one or more epigenetic values. In some examples, the epigenetic values may be measured according to a DNA epigenetic assay technique (e.g., bisulfite sequencing, pyrosequencing, microarray scanning, chIP-on-chip) and the target DNA locus may be a DNA locus associated with a failed, unavailable, or inaccurate assay (e.g., microarray probe).

In an additional or alternate example, a measured epigenetic value may be available that is associated with the target DNA locus. In such an example, the techniques discussed herein may be used to determine a confidence that the measured epigenetic value is accurate based at least in part on a difference between the measured epigenetic value and the estimated epigenetic value determined by the ML model. The ML model discussed herein may thereby improve the art by providing a faster and additional means by which to estimate an epigenetic value at a DNA locus and/or may be part of a system that triggers an alert when a probe has failed and/or may be inaccurate. In some instances, the techniques discussed herein may transmit a notification that a probe has failed (e.g., display a notification via a user interface of a machine running the ML model or in communication with a machine running the ML model) and/or may have generated an inaccurate measurement based at least in part on determining that a confidence associated with the target DNA locus (and the probe) is less than a threshold confidence (e.g., which may be determined based at least in part on a difference between a measured epigenetic value determined in association with the probe and an estimated epigenetic value determined by the ML model). In additional or alternate examples, the ML model may be trained to output a confidence and/or confidence interval in association with the estimated epigenetic value that quantifies a likelihood the estimated epigenetic value is accurate. In some examples, the confidence may be a posterior probability.

The techniques discussed herein may comprise training multiple ML models using different training data sets and/or different training targets, such that different ML models may receive different inputs and/or generate different outputs. In some examples, training data sets (i.e., the observed data) for different ML models may be differentiated based at least in part on biological sample type (e.g., a first training data set may comprise first epigenetic data derived from a blood sample, a second training data set may comprise second epigenetic data derived from a saliva sample), epigenetic data type, an assay type by which the epigenetic data was determined (e.g., a first assay that measures methylation levels at 27,578 CpG dinucleotides, such as the Illumina Infinium HumanMethylation27 BeadChip (commonly referred to as a 27k methylation array), a 450k array, an 850k array, e.g., the Illumina EPIC BeadChip). In an additional or alternate example, the training target, i.e., the DNA locus(i) for which the ML model is trained to output an estimated epigenetic level, may be varied between different ML models. In an additional or alternate example, the ML model(s) described herein may receive additional or alternative epigenetic data as input, such as, for example, acetylation, histone protein modifications, phosphorylation, sumoylation, and/or the like.

For example, differentially training the multiple ML models may result in a first group of ML models that are all trained to output an estimated epigenetic value for a first DNA locus and a second group of ML models that are all trained to output an estimated epigenetic value for a second DNA locus. However, the first group of ML models may comprise a first ML model trained on epigenetic data derived from a 27k array of DNA gathered from a saliva sample, a second ML model trained on epigenetic data derived from a 450k array of DNA gathered from a saliva sample, a third ML model trained on epigenetic data derived from a 27k array of DNA gathered from a blood sample, and so on. The second group of ML models may similarly include different ML models configured to receive different inputs.

In some examples, according to the techniques discussed herein, even though a first ML model and a second ML model of the first group may both be trained to generate an estimated epigenetic value for a first DNA location, the first ML model may be configured to receive an epigenetic values associated with a first set of DNA loci whereas the second ML model may be configured to receive epigenetic values associated with a second set of DNA loci. This differentiation between the DNA loci received as input by the two ML models may occur as a result of the training techniques discussed herein.

In some examples, the different ML models (of a same or different group) may comprise different architectures and/or hyperparameters compared to one another. For example, training a first ML model may comprise training a plurality of ML models having different architectures and/or hyperparameters and selecting the first ML model from among the plurality of ML models based at least in part on an accuracy, recall, size, and/or processing speed associated with the first ML model.

The techniques may comprise receiving epigenetic data associated with a subject (e.g., by any suitable assay), receiving an indication of a target DNA locus, determining a subset of the epigenetic data that is associated with an ML model for generating an estimated epigenetic value for the target DNA locus (e.g., this may include determining epigenetic values corresponding to DNA loci for which the ML model was trained), providing the subset to the ML model, and receiving an estimated epigenetic value associated with the target DNA locus from the ML model. The technique may additionally or alternatively comprise selecting an ML model associated with the target DNA locus (and/or associated with an assay type and/or biological sample type from which the epigenetic data was determined) from among multiple ML models.

In some examples, an ML model may be trained to output a confidence that the estimated epigenetic data is accurate. For example, the confidence may be a posterior probability that the ML model may learn to output and/or the posterior probability may be deterministically determined based at least in part on a probability distribution and the subset of epigenetic data provided to the ML model. In some examples, training may comprise determining the probability distribution associated with a target DNA locus based at least in part on the epigenetic values associated with the target DNA locus and the subset of DNA loci in the training data sets.

In some examples, the techniques discussed herein improves the state of the art by providing a technique to obtain an estimated epigenetic value for a DNA locus when a probe for the DNA locus has failed, is inaccurate, or is unavailable. Depending on the assay type, target DNA locus, and/or biological sample type, the ML models discussed herein may achieve $R^2$ value over 0.9. For those ML models discussed herein that have high (e.g., over 0.79, over 0.9) $R^2$ values, depending on the application, the techniques described herein may obtain a sufficient estimation of an epigenetic level at a DNA locus that a cheaper, easier and/or quicker to process assay type may be used to generate the epigenetic data discussed herein. For example, in at least one example, the epigenetic value for a target DNA locus may be measured using an 850k array, but a probe for measuring the target DNA locus may not exist on a 27k array. However, the ML model for the target DNA locus trained using a training data set generated using the 27k array may have an adequate AUC. The technique thereby provides a method of testing the target DNA locus using the 27k array.

In some examples, the techniques discussed herein may provide a method by which to detect and/or determine a likelihood of an assay failure and/or inaccuracy, e.g., based at least in part on a difference between a measured epigenetic value determined by an assay and an estimated epigenetic value output by an ML model, where the estimated epigenetic value is associated with a same DNA locus as the measured epigenetic value.

The term, "array" or "microarray" as used herein means a tool designed to detect the presence of specific genetic sequences or alleles (some may represent methylated or unmethylated cytosines) in a plurality of genomic regions at the same time via the use of a plurality of probes that are fixed at set positions on a solid surface. The term, "probes" as used herein means a sequence of nucleic acids that have base pair complementarity to a sequence of interest. The term, "sequencing" as used herein means the process of determining a nucleic acid sequence through a variety of possible methods and technologies. The term, "synthetic probes" as used herein means a software and/or hardware probe comprise a machine learning model designed to predict a status/value associated with a target DNA locus.

Example Operations

Figure 1:
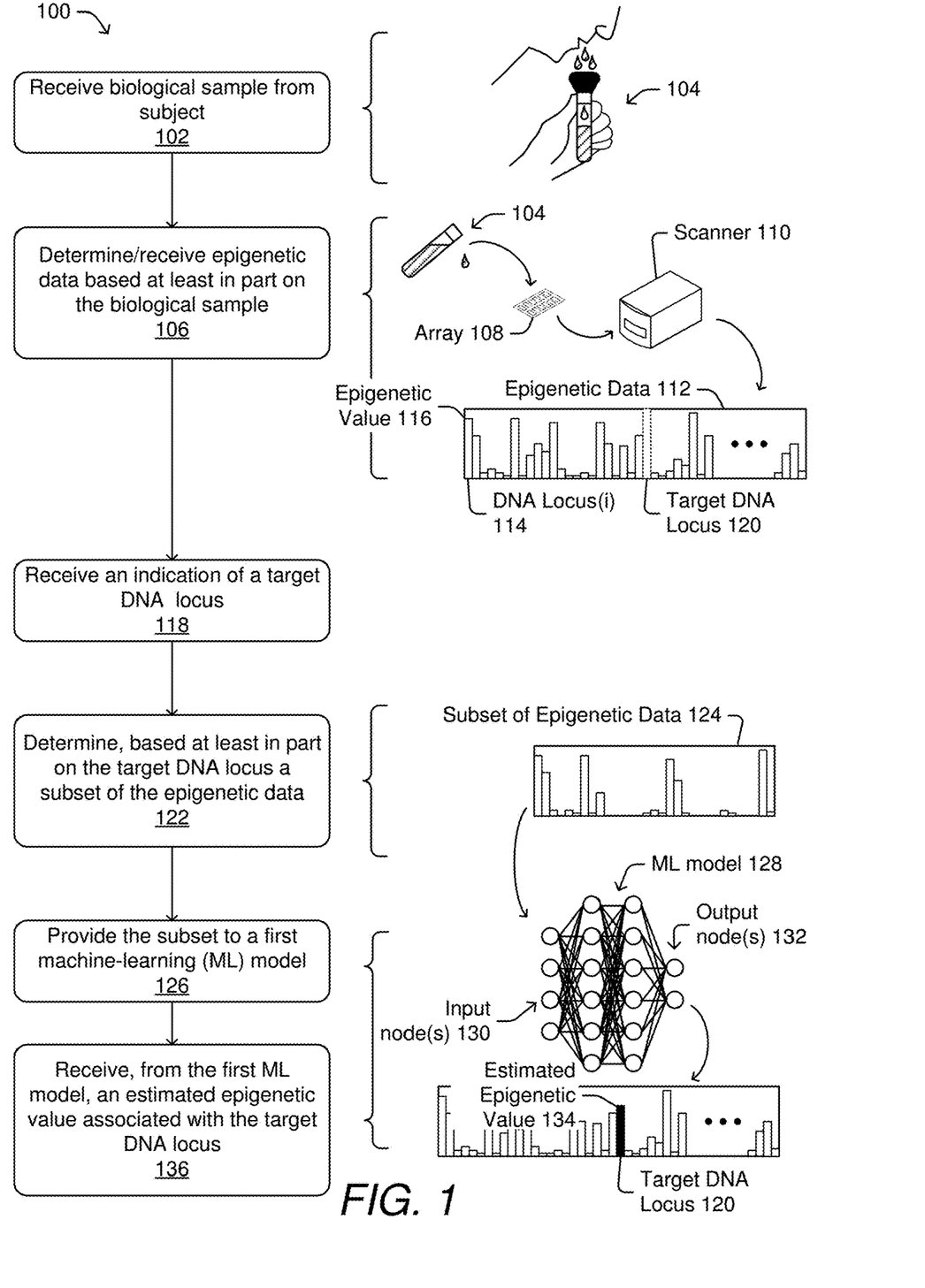
FIG. 1 illustrates a pictorial flow diagram of an example process for determining, by an ML model trained according to the techniques discussed herein, an estimated risk classification, biochemical state, and/or medical condition using methylation data associated with a subject.
Figure 2A:
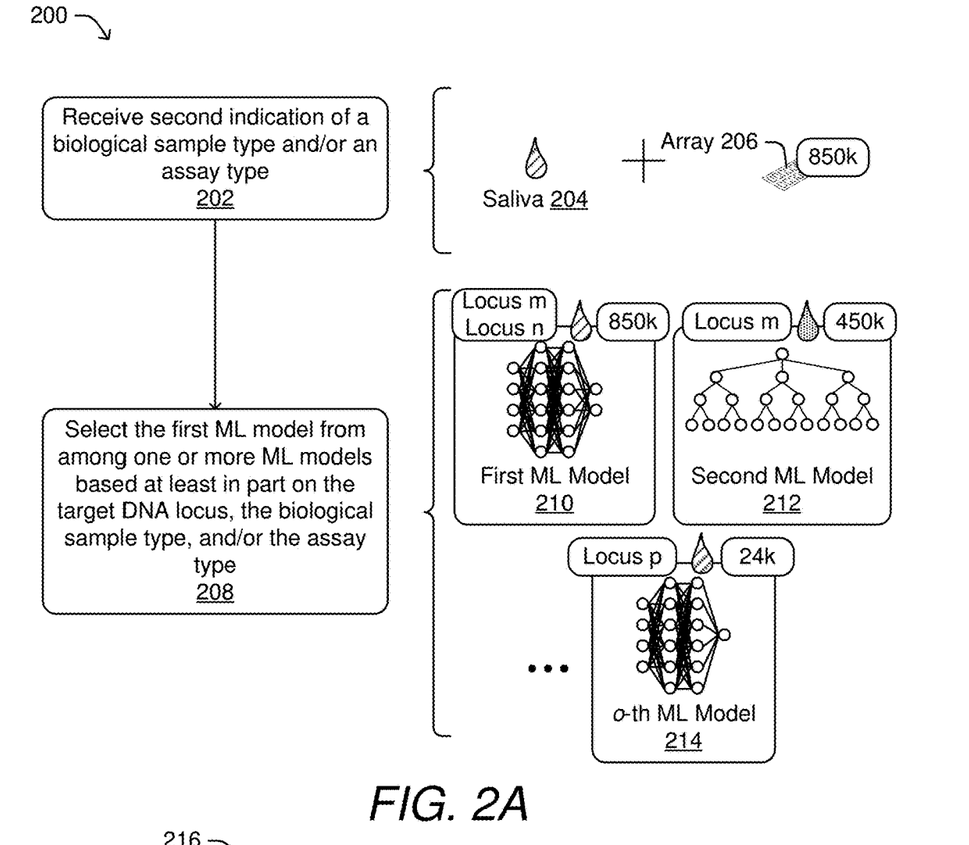
FIG. 2A illustrates a pictorial flow diagram of an example process for selecting an ML model from among multiple ML models for determining an estimated methylation value based at least in part on the target DNA locus, the biological sample type, and/or the assay type.
Figure 2B:
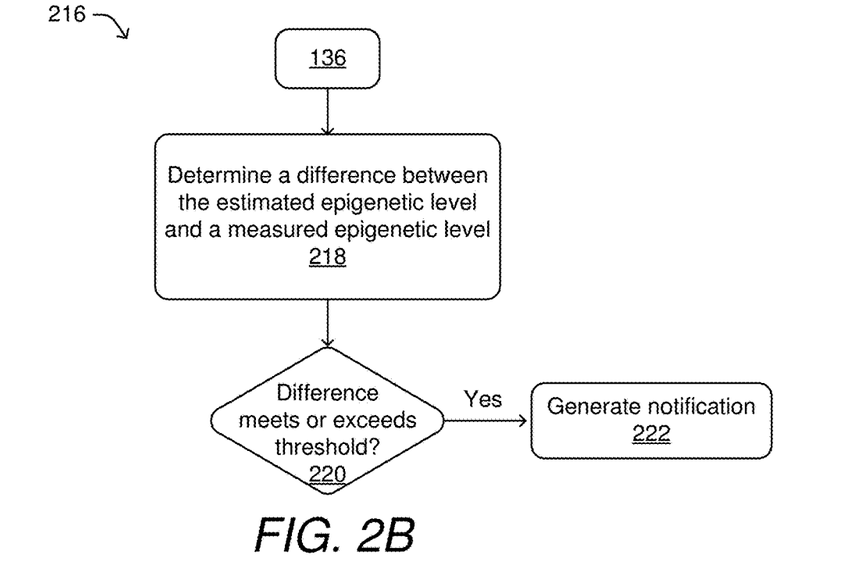
FIG. 2B illustrates a flow diagram of an example quality control and/or probe inaccuracy detection process.
Figure 3:
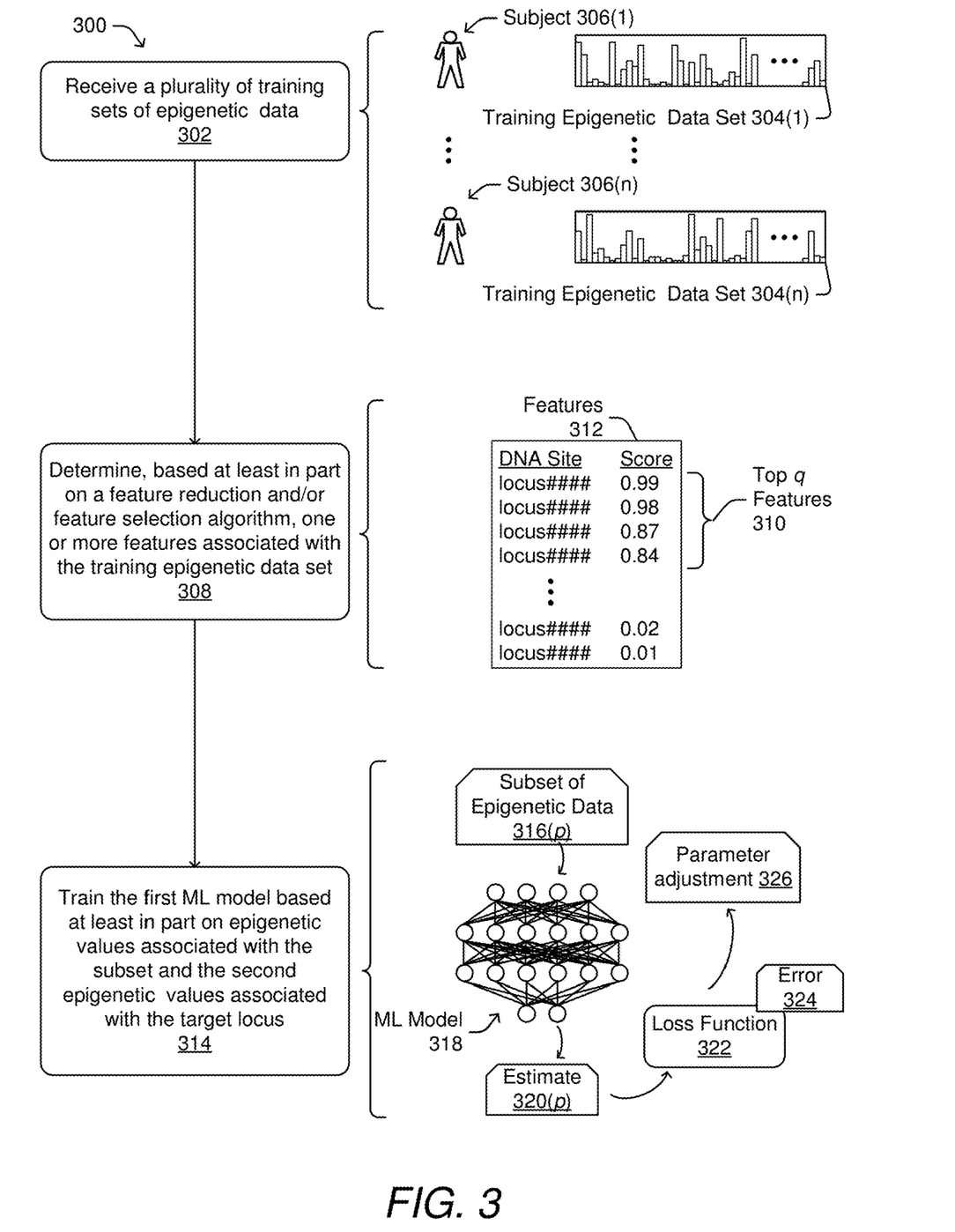
FIG. 3 illustrates a pictorial flow diagram of an example process for training at least one of the ML models discussed herein.

FIG. 1 illustrates a pictorial flow diagram of an example process 100 for determining an estimated epigenetic value associated with a target DNA locus by an ML model. FIGS. 1-3 illustrate example processes in accordance with embodiments of the disclosure. These processes are illustrated as logical flow graphs, each operation of which represents a sequence of operations that can be implemented in hardware, software, or a combination thereof. In the context of software, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described operations can be combined in any order, in parallel to implement the processes, and/or may be performed as independent processes.

At operation 102, example process 100 may comprise receiving a biological sample 104 from the subject, according to any of the techniques discussed herein. For example, the biological sample may comprise one or more samples of tissue (e.g., skin, muscle, bone, adipose tissue, microbiome) and/or one or more samples of bodily fluid (e.g., saliva, whole blood, serum, plasma). The biological sample 104 may comprise DNA and/or be selected such that the biological sample 104 is likely to comprise DNA. In some examples, DNA containing biological samples can be obtained from an individual via saliva collection, as depicted in FIG. 1, although any other method of biological sample collection may be performed, such as a blood draw.

In some examples, receiving the biological sample may additionally or alternatively comprise isolating cells of the biological sample 104 by individual cell types. For example, the different cell types may include stem cells, erythrocytes, granulocytes (e.g., neutrophils, eosinophils, basophils), agranulocytes (e.g., monocytes, lymphocytes), platelets, neurons, neuroglial cells, skeletal muscle cells, cardiac muscle cells, smooth muscle cells, chondrocytes, keratinocytes, osteoclasts, osteoblasts, melanocytes, Merkel cells, Langerhans cells, endothelial cells, epithelial cells, adipocytes, spermatozoa, ova, and/or the like.

At operation 106, example process 100 may comprise determining and/or receiving epigenetic data based at least in part on the biological sample 104, according to any of the techniques discussed herein. For example, determining the epigenetic data may comprise processing the biological sample 104 by 1) extracting genomic DNA from cells (e.g., epithelial cells, white blood cells) present in the biological sample 104 via one of several methods (e.g., salting out, phenol-chloroform, silica gel, benzyl-alcohol, magnetic beads), 2) denaturing the extracted DNA, 3) incubating the denatured DNA in a bisulfite containing compound and thermocycling at set temperatures and intervals, 4) purifying, desulphonating, and/or neutralizing of the bisulfite converted genomic DNA, and/or 5) measuring methylation levels through DNA sequencing and/or microarray analysis. In general, this process of bisulfite sequencing differentiates and detects unmethylated versus methylated cytosines by converting unmethylated cytosine base pairs to uracil, while methylated cytosines remain. In additional or alternative examples, the DNA may not undergo bisulfite conversion and may be analyzed without alteration (steps 3-4).

In at least one example, DNA prepared according to steps 1-4 may be applied to a microarray, such as array 108, which may comprise a fluorophore-, silver-, and/or chemiluminescent-labeled probe for indicating successful/failed binding of the probe to a particular DNA locus, which may indicate that the DNA locus is methylated/unmethylated and/or a level of methylation associated with the DNA locus. For example, array 108 may comprise a microarray chip (e.g., Illumina MethylationEPIC BeadChip (850k array), IlluminaHumanMethyalation450 BeadChip (450k array), IlluminaHumanMethyalation27 BeadChip (27k array), chromatin immunoprecipitation (ChIP) microarray), a DNA chip, or a biochip. A scanner 110 may detect and quantify an intensity of the classification output (e.g., an intensity of the fluorescence associated with a probe) to determine a binary (unmethylated/methylated) or continuous (methylation level) indication of methylation at the DNA locus. In an additional or alternate example, any other method of processing the DNA may be performed (e.g., methylation specific polymerase chain reaction, methyl-sensitive cut counting, luminometric methylation assay, pyrosequencing).

Although the discussion herein discusses methylation data, it is understood that other epigenetic data such as, for example, acetylation, histone protein modifications, phosphorylation, sumoylation, and/or the like may be used to train the ML model(s) discussed herein (e.g., the ML model(s) may receive methylation data as input or any other type of epigenetic data). Epigenetic alterations to the genome comprise a host of different biochemical changes to DNA and proteins associated with it. For example, the cytosine residues of DNA may be methylated, which when methylated near regions that control gene expression (e.g., promoter regions), may alter gene expression. Another example is the modification of lysine tails on histone proteins. DNA wraps around histone proteins to form its superstructure. The modification of these tails may change the confirmation of DNA to make it more or less accessible for transcription and gene expression. These examples are not exhaustive and more are contemplated.

Regardless of what type of epigenetic data is obtained or used herein, FIG. 1 depicts an example representation of epigenetic data 112, determined by whatever means, which may comprise an epigenetic value 116 associated with a DNA locus 114. The depicted example shows additional epigenetic values associated with other DNA loci as well. In additional or alternate examples, measured and/or estimated values may be associated with any kind of epigenetic modifications.

In some examples, the epigenetic values of the epigenetic data 112 may be normalized (e.g., quantile normalization, subset-quantile within array normalization (SWAN), beta-mixture quantile method, dasen, normal-exponential out-of-band (NOOB), single sample NOOB (ssNOOB)) and/or otherwise pre-processed (e.g., background correction, dye bias correction, pre-filtered to remove epigenetic values and DNA loci associated with n % of samples having detection p-values below a detection threshold, e.g., 0.05, 0.001, 0.0001, wherein n is a positive integer, e.g., 50, 30, 75). In some examples, the epigenetic value 116 may be a binary indication of methylation or unmethylation, or the epigenetic value 116 may comprise a Beta-value and/or M-value. Epigenetic "value" is also referred to herein as an epigenetic level. A Beta-value may be the ratio of the methylated probe intensity and the overall intensity (sum of methylated and unmethylated probe intensities). For example, the Beta-value for an i-th DNA locus may be defined as:

$$\beta_i = \frac{\max(y_{i,methy}, 0)}{\max(y_{i,unmethy}, 0) + \max(y_{i,methy}, 0) + \alpha} \quad (1)$$

where $y_{i,methy}$ and $y_{i,unmethy}$ are the intensities measured by the i-th methylated and unmethylated probes, respectively, and $\alpha$ is an offset (e.g., default value of 100) to regularize the Beta-value when the methylated and unmethylated probe intensities are low. A Beta-value of 0 indicates that all copies of the DNA locus in the sample were completely unmethylated and vice versa (full methylation of all copies of DNA locus in sample) for a Beta-value of 1.

The M-value may be the log 2 ratio of the intensities of methylated probe versus unmethylated probe. For example, the M-value for an i-th DNA locus may be defined as:

$$M_i = \log_2\left(\frac{\max(y_{i,methy}, 0) + \alpha}{\max(y_{i,unmethy}, 0) + \alpha}\right) \quad (2)$$

where α is an offset (e.g., default value of 1) to decrease the sensitivity of the equation to intensity estimation errors. An M-value close to 0 indicates a similar intensity between the methylated and unmethylated probes associated with a DNA locus, which means that the DNA locus may be approximately half methylated, assuming the intensity data is normalized. A positive M-value indicates more molecules are methylated than unmethylated, whereas the opposite is true of negative M-values.

The DNA locus 114 may be related to one or more DNA base pairs. For example, a DNA locus 114 may comprise an individual DNA base pair at a particular genomic location or may be a genomic region such as a CpG island, a promoter, an enhancer, an activator, a repressor, a transcription start sites, and/or the like. While these regions are indicated, others are contemplated. For example, the DNA locus may comprise non-coding RNA molecules (nc-RNAs) such as micro RNA (miRNA), small interfering RNA (siRNA), piwi-interacting RNA (piRNA), and/or long non-coding RNA (lncRNA). These nc-RNAs may also be measured through sequencing.

At operation 118, example process 100 may comprise receiving an indication of a target DNA locus 120 from the epigenetic data 112, according to any of the techniques discussed herein. For example, the target DNA locus 120 may be received responsive to detecting that a probe (of array 108) failed, is inaccurate (e.g., a probe that tests the target DNA locus 120 may be associated with a low accuracy), and/or unavailable (e.g., the array 108 may not include a probe that measures an epigenetic level at the target DNA locus 120). In some examples, the target DNA locus 120 may additionally or alternatively be received responsive to user selection at a user interface of a computing device, such as the scanner 110 and/or any other computing device.

At operation 122, example process 100 may comprise determining a subset 124 of the epigenetic data 112, according to any of the techniques discussed herein. For example, determining the subset of the epigenetic data 112 may be based at least in part on input accepted by an ML model and/or the particular ML model selected according to the techniques discussed herein (e.g., in regard to example process 200). In some examples, the input accepted by an ML model may be defined by an input criterion stored at a computing device that causes storage and/or execution of the ML model or is communicatively coupled to cause inputs to be provided to the ML model. For example, the input criterion may specify a subset of DNA loci and the subset 120 of the epigenetic data 112 may comprise epigenetic values associated with the subset of DNA loci.

For example, determining, based at least in part on the target DNA locus, a subset 124 of the epigenetic data 112 may be based at least in part on input accepted by an ML model and/or the particular ML model selected according to the techniques discussed herein (e.g., in regard to example process 200). In some examples, the input accepted by an ML model may be defined by an input criterion stored at a computing device that causes storage and/or execution of the ML model or is communicatively coupled to cause inputs to be provided to the ML model. For example, the input criterion may specify a subset of DNA loci and the subset 124 of the epigenetic data 112 may comprise epigenetic values associated with the subset of DNA loci.

In some examples, determining to include epigenetic data associated with a DNA locus in the subset 124 may additionally or alternatively comprise determining a proximity of the DNA locus to the target DNA locus and/or determining a relatedness of the DNA locus to the target DNA locus based at least in part on a correlation. For example, determining the proximity to the target DNA locus may comprise determining a number of base pairs separating the DNA locus from the target DNA locus. In other words, the subset may be determined based at least in part on where the target DNA locus 120 is in the DNA.

Operation 122 may additionally or alternatively comprise selecting a DNA locus for inclusion in the subset based at least in part on determining a distribution pattern associated with the target DNA locus (e.g., the distribution pattern may be determined from a plurality of epigenetic values received from different subjects in association with the target DNA locus). For example, operation 122 may comprise determining a distribution pattern associated with target DNA locus may comprise determining whether the target DNA locus is unimodal, bimodal, trimodal, and/or the like, and/or a variance associated with a distribution of values associated with the target DNA locus. In some examples, operation 122 may comprise classifying the target DNA locus as being unimodal and having a high variance, unimodal and having a low variance, bimodal, trimodal, and/or multimodal. For example, selecting one or more DNA loci for inclusion in the subset 124 may comprise ranking the DNA loci based at least in part on a modality and/or variance of the DNA loci.

At operation 126, example process 100 may comprise providing the subset 124 as input to an ML model 128, according to any of the techniques discussed herein. For example, the ML model 128 may comprise a regressor (e.g., an ML model that outputs a value, such as an epigenetic value or an estimated epigenetic value). In some examples, the ML model 128 may be learned according to supervised, unsupervised, or semi-supervised learning techniques.

Figure 4:
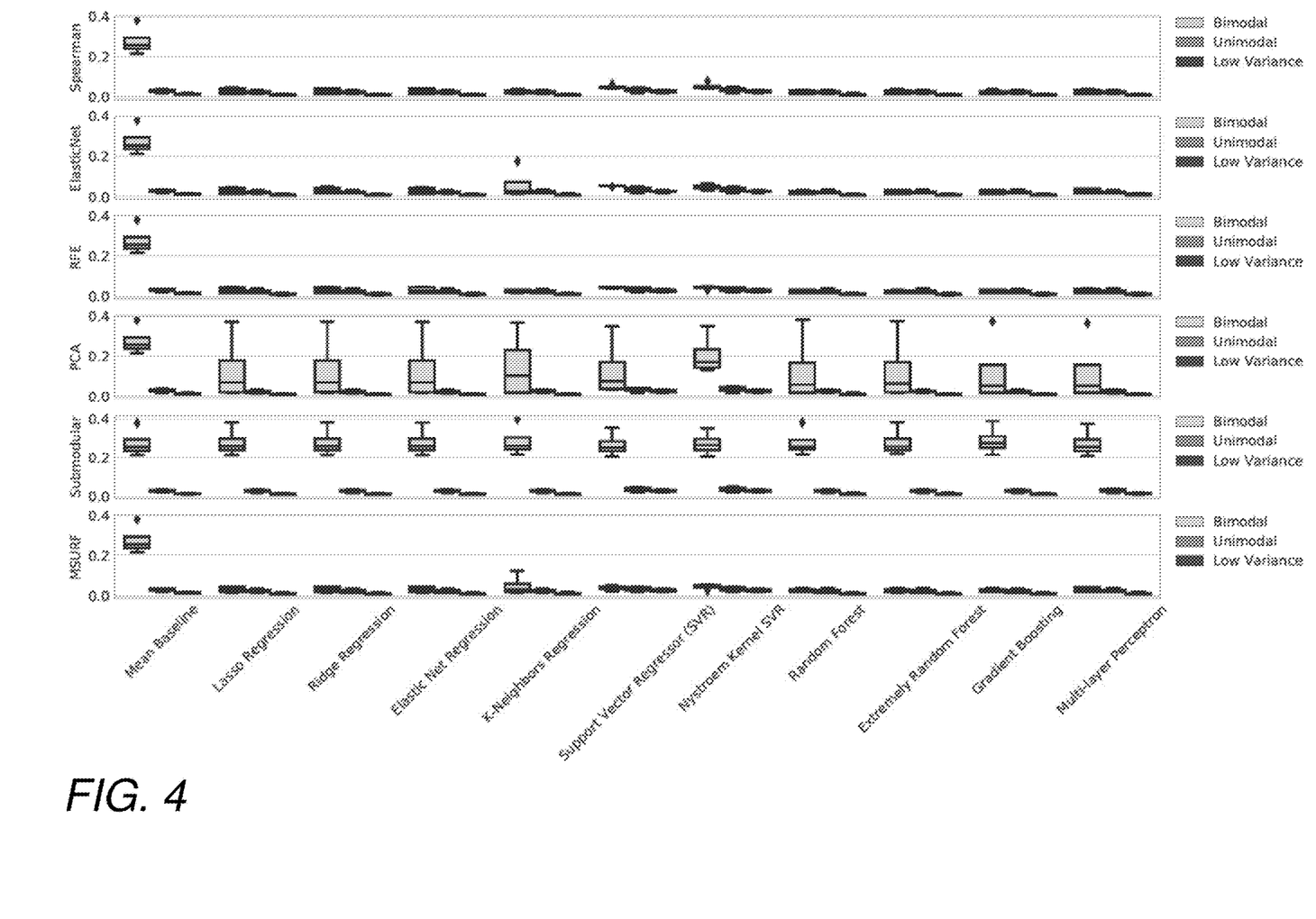
FIG. 4 illustrates a graph of mean average error rates associated with different feature selection algorithms (depicted on the y-axis) for different machine-learning models (depicted on the x-axis) and different distribution patterns.
Figure 5:
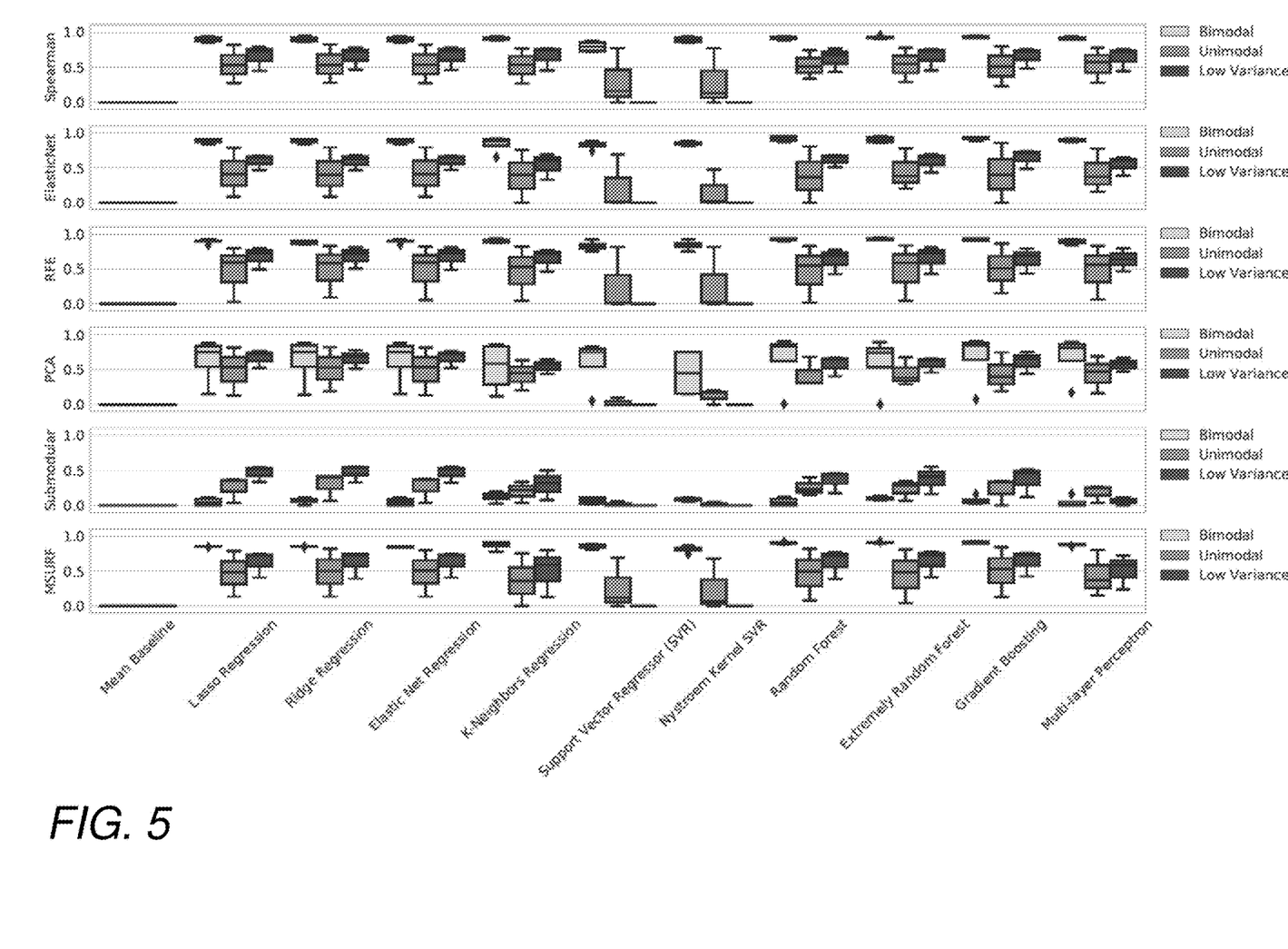
FIG. 5 illustrates a graph of Spearman rank correlation coefficients associated with different feature selection algorithms (depicted on the y-axis) for different machine-learning models (depicted on the x-axis) and different distribution patterns.

For example, FIG. 1 depicts the ML model 128 as a multi-layer perceptron (MLP) having an input layer comprising input node(s) 130, two hidden layers (intervening the input node(s) 130 and the output node(s) 132), and an output layer comprising output node(s) 132. In some examples, the number of input node(s) 130 may equal the number of DNA loci of the subset 124, and the number of output node(s) 130 may correspond to a number of outputs that the ML model 128 is trained to output. For example, the ML model 128 may be trained to output an estimated epigenetic value 134 for a target DNA locus 120. The ML model 128 may additionally or alternatively output a confidence score and/or confidence interval associated with the output. In at least one example, a first output node of the output node(s) 130 may output an estimated epigenetic value 134 and a second output node of the output node(s) 132 may output a confidence and/or confidence interval associated with the risk classification. It is understood that a MLP is merely one example of any of a plurality of types of ML models that may be used according to the techniques discussed herein. In additional or alternate examples, the ML model 128 may comprise a spearman correlator, a random forest, and/or the like. For example, FIG. 4 depicts mean average error rates for and FIG. 5 depicts Spearman rank correlation coefficient for different feature selection algorithms (displayed on the y-axis) and machine-learning models (displayed on the x-axis) for DNA loci of different distribution patterns (i.e., bimodal, unimodal, low variance).

At operation 136, example process 100 may comprise receiving, from the ML model, the estimated epigenetic value 134 according to any of the techniques discussed herein. As discussed above, the output may be indicated by a value (e.g., a beta-value and/or an M-value). The output may additionally or alternatively comprise a confidence and/or confidence interval associated with the value.

FIG. 2A depicts a pictorial flow diagram of an example process 200 for selecting an ML model from among multiple ML models for determining an estimated epigenetic value based at least in part on the target DNA locus, the biological sample type, and/or the assay type.

At operation 202, example process 200 may comprise receiving a second indication of a biological sample type (e.g., saliva 204, blood, buccal cells) and/or assay type (e.g., array 206), according to any of the techniques discussed herein. In some examples, a specialized computing device, such as a scanner, may provide the indication in a metadata file associated with the epigenetic data. FIG. 2 depicts saliva 204 as an example biological sample type and an 850k microarray 206, although any other biological sample type and/or assay type are contemplated.

At operation 208, example process 200 may comprise selecting an ML model from among one or more ML models based at least in part on biological sample, according to any of the techniques discussed herein. For example, each ML model may have an input criterion associated therewith that may indicate a type of input the ML model was trained to receive and a type of output the ML model was trained to output. Operation 208 may comprise searching over the input criteria associated with the ML model(s) to determine an ML model trained to output data associated with a target DNA locus and that receives input associated with the biological sample type and/or assay type from which the epigenetic data (for input) was determined, although, in some examples, an ML model may be trained generally (e.g., the training data used to train the ML model comprised multiple types of biological sample types and/or multiple assay types) and/or agnostically (e.g., without receiving an indication of the type of data being input). In some examples, the array type may be a minimum array type—in other words, the ML model may be trained to receive epigenetic data derived from a first array type or greater array, according to a hierarchy of arrays (e.g., 850k array provides epigenetic data for more DNA loci than a 450k array, which provides epigenetic data for more DNA loci than a 27k array; epigenetic data determined by a 850k array may be used for an ML model trained to receive 27k array epigenetic data).

For example, and according to the example depicted in FIG. 2A, the first ML model 210 may be trained to output an estimated epigenetic for DNA locus m and DNA locus n using epigenetic data determined using a 850k array and/or a saliva sample, the second ML model 212 may be trained to output an estimated epigenetic value for DNA locus m using epigenetic data determined using a 450k array (and any sample type), and/or the o-th ML model 214 may be trained to output an estimated epigenetic value for a DNA locus p using epigenetic data determined using a 24k array and/or a blood sample.

As discussed further herein, two different ML models of the plurality of ML models may be a same or different type (e.g., the first ML model 210 and the o-th ML model 214 are both depicted as being MLPs whereas the second ML model 212 is depicted as being a decision tree) and may comprise classifiers and/or regressors. ML models of a same type may have the same or different hyperparameters. Hyperparameters associated with a component of an ML model may define properties of the structure of the ML model such as, for example, a number and/or order of layers and/or nodes of the ML model, a number of nodes and/or a maximum depth of the ML model (e.g. a maximum number of child nodes in a decision tree, a maximum number of filters), a number of decision trees in a forest, a number of features considered by a tree when splitting a node, use of a Gini impurity or entropy (or gain), a dimension of filters of the layers and/or nodes, spatial extent, stride, amount of zero padding, input size (e.g., tensor, having dimensions $W_1 \times H_1 \times D_1$, or any other number of dimensions) and/or type (e.g., raw epigenetic data, normalized epigenetic data, tensor received from a previous component of an ML pipeline), output size and/or type (e.g., tensor having dimensions $W_1 \times H_1 \times D_1$ or $W_2 \times H_2 \times D_2$, a first dimension of a tensor indicating one or more risk classifications, one or more biochemical state values, one or more ICD-9 codes (or other medical condition indications), or one or more medical condition values; a second dimension indicating one or more confidence scores associated, respectively, with data indicated by the first dimension of the first tensor) and/or the like associated with a component of the ML model.

Although two different ML models of the plurality of ML models may have the same or similar hyperparameters, training the ML models based at least in part on different input data and/or to determine two different kinds of input may cause parameters associated with the two ML models to be different. A parameter, in contrast to a hyperparameter, may comprise any parameter that is modified during training such as, for example, a weight associated with a layer or components thereof (e.g., a filter, node). Although various examples of hyperparameters are given herein, it is contemplated that one or more of the hyperparameters may be parameters, depending on the training method.

In some examples, example process 200 may be used to reconstruct a larger assay from a smaller assay by using measured epigenetic values associated with a smaller assay to estimate one or more epigenetic values associated with the larger assay. This assay extension may comprise selecting a set of ML models to estimate at least part of an assay that tests a larger set of DNA loci than an assay by which the measured epigenetic data was received. For example, if a 27k array was used to determine a set of epigenetic data, example process 200 may comprise selecting a sufficient set of ML models to generate estimated epigenetic values for DNA loci corresponding to a 450k array. The number of ML models selected may be equal to or less than the additional number of DNA loci for which epigenetic values are estimated beyond the original set of DNA loci associated with the smaller assay. In other words, one of the plurality of ML models may be configured to generate an estimated epigenetic value for one or more DNA loci.

FIG. 2B illustrates a flow diagram of an example process 216 for detecting an inaccurate and/or failed probe and/or determine a likelihood that a probe failed and/or is inaccurate. Example process 216 may be conducted by a computing device such as, for example, a scanner and/or any other computing device. Example process 216 may comprise operation 136, which may comprise receiving an estimated epigenetic value associated with a target DNA locus from at least one of the ML models discussed herein. Example process 216 may additionally or alternatively comprise receiving a measured epigenetic value associated with the target DNA locus. For example, receiving a measured epigenetic value associated with the target DNA locus may be part of operation 106.

At operation 218, example process 216 may comprise determining a difference between the estimated epigenetic level and the measured epigenetic level, according to any of the techniques discussed herein. For example, determining the difference may comprise determining a difference in Beta-value, M-value, and/or the like. In some examples, determining the difference may comprise determining a residual between the estimated epigenetic level and the measured epigenetic level. In an additional or alternate example, operation 218 may comprise determining a likelihood (e.g., a posterior probability) that the measured epigenetic level is inaccurate based at least in part on the estimated epigenetic level and/or the measured epigenetic level).

At operation 220, example process 216 may comprise determining whether the difference between the estimated epigenetic level and the measured epigenetic level meets or exceeds a threshold (or in an additional or alternate example whether the likelihood meets or exceeds a likelihood threshold), whether the likelihood meets or exceeds a threshold likelihood), according to any of the techniques discussed herein. For example, operation 220 may fundamentally determine whether the measured epigenetic value is likely to be inaccurate and/or attributable to a failed probe of an assay, based at least in part on the difference determined at operation 218. If the difference (and/or likelihood) meets or exceeds the threshold, the example process 216 may transition to operation 222, otherwise the example process 216 may take no action.

At operation 222, example process 216 may comprise generating a notification, according to any of the techniques discussed herein. Generating the notification may comprise transmitting a message, causing a user interface to indicate that measured epigenetic value associated with the target DNA locus may be inaccurate and/or that a probe associated therewith may have failed, and/or the like.

In an additional or alternate example, example process 216 may comprise determining a likelihood and/or an indication that a respondent may have falsified information. For example, a respondent may provide an indication that the respondent does or does not have a medical condition; take a pharmaceutical; use alcohol, nicotine, or other drugs; and/or the like. In some examples, a response may be associated with an average epigenetic value and operation 220 may comprise determining a difference between an estimated epigenetic level and/or a measured epigenetic level and the average epigenetic value. If the difference meets or exceeds a threshold difference, example process 216 may comprise determining a score based at least in part on the difference and/or generating notification that the respondent may have falsified information. In some examples, the score may comprise a likelihood, such as a posterior probability.

For example, the respondent may transmit (e.g., via a network interface) an indication that the respondent does not use alcohol. The average epigenetic value associated with no alcohol use may be determined based at least in part on epigenetic data associated with subjects that do not use alcohol and/or have not used alcohol within specified time period. A difference that meets or exceeds a threshold difference between the average epigenetic value and the measured and/or estimated epigenetic value may be associated with likely falsification.

Example Training Operations

FIG. 3 illustrates a pictorial flow diagram of an example process for training at least one of the ML models discussed herein. The training techniques may vary based at least in part on a type and/or hyperparameters associated with ML model to be trained. In some examples, an ensemble of ML models may be trained and a best-performing ML model may be selected from among the ensemble (e.g., where best-performing may be based at least in part on accuracy, recall, size, storage size, and/or speed).

At operation 302, example process 300 may comprise receiving a plurality of training sets comprising epigenetic data, according to any of the techniques discussed herein. FIG. 3 depicts training epigenetic data sets 304(1)-(n) associated, respectively, with subjects 306(1)-(n), where n is a positive integer. For example, training epigenetic data set 304(n) may be determined from a biological sample received from subject 306(n) and training epigenetic data set 304(1) may be determined from a biological sample received from subject 306(1).

At operation 308, example process 300 may comprise determining, based at least in part on a feature reduction and/or feature selection algorithm, one or more features associated with the training epigenetic data set(s), according to any of the techniques discussed herein. The features selected according to operation 308 may comprise a subset of DNA loci, a biological sample type, an assay type, and/or the like, although in at least one example, the features comprise a subset of DNA loci, as FIG. 3 depicts. Operation 308 may, in some examples, select a top q features 310 from a ranked list of features 312 (where q is a positive integer), ranked according to scores determined based at least in part on a feature selection and/or feature reduction algorithm. The feature reduction and/or feature selection algorithm may comprise, for example, Spearman's rank correlation with the target label, features selection via ElasticNet, recursive feature elimination (RFE) (e.g., using an additive feature attribution method, such as by assigning an importance score, e.g., via Shapley Additive exPlanations (SHAP) LIME, DeepLIFT, layer-wise relevance propagation, and/or the like, to a feature based at least in part on an estimate determined based on the feature), principal components analysis (PCA), matrix factorization (e.g., SVD++), diversity selection based on latent space from a matrix factorization, a Relief algorithm (e.g., SURF, SURF*, MultiSURF, MultiSURF*), or a combination thereof.

In some examples, operation 308 may additionally or alternatively comprise pre-processing and/or post-processing operations, such as a second feature reduction operation (e.g., first feature reduction operation may reduce the number of DNA loci from tens of thousands to thousands, and second feature reduction operation may reduce the number of DNA loci to hundred), normalization (e.g., using quantile normalization, NOOB), scaling, smooth transformation, standardization of the data, and/or the like.

In some examples, operation 308 may additionally or alternatively comprise pre-processing and/or post-processing operations, such as a second feature reduction operation (e.g., first feature reduction operation may reduce the number of DNA loci from tens of thousands to thousands, and second feature reduction operation may reduce the number of DNA loci to hundred), normalization (e.g., using quantile normalization, NOOB), scaling, smooth transformation, standardization of the data, and/or the like.

At operation 314, example process 300 may comprise training the ML model based at least in part on epigenetic values associated with a subset of the epigenetic data and/or target label data, according to any of the techniques discussed herein. Operation 314 may comprise iteratively providing training data 316(p) to an ML model 318, receiving an estimate 320(p), and tuning the ML model based at least in part on a difference between the estimate 320(p) and a ground truth associated with the subset of epigenetic data 316(p) according to a supervised, or semi-supervised learning technique and/or a difference between the estimate and some indication of deviation from the observed data (e.g., an average distance to the medoid of a cluster) for an unsupervised learning technique. For example, for a p-th set of training data and/or a p-th iteration of training, operation 314 may comprise determining a subset 316(p) of the training epigenetic data set 304(n) based at least in part on the top q features determined at operation 308 (e.g., identifying the methylation levels associated with the q DNA loci determined as part of the top q features at operation 308). The subset 316(p) may be provided as input to the ML model 318. In some examples, the subset 316(p) may be standardized, normalized, scaled, smoothly transformed, and/or the like before being provided as input.

The ML model 318 may comprise, for example, a support vector machine (SVM) (e.g., Nystroem Kernel SVM, radial basis function (RBF) kernel SVM), a regression algorithm (e.g., ordinary least squares regression (OLSR), linear regression, logistic regression), decision tree algorithms (e.g., classification and regression tree (CART), iterative dichotomiser 3 (ID3), Chi-squared automatic interaction detection (CHAID), decision stump, conditional decision trees, LightGBM, gradient-boosting machines (GBM), gradient boosted regression trees (GBRT), random forest), Bayesian algorithms (e.g., naïve Bayes, Gaussian naïve Bayes, multinomial naïve Bayes, average one-dependence estimators (AODE), Bayesian belief network (BNN), Bayesian networks), clustering algorithms (e.g., k-means, k-medians, expectation maximization (EM), hierarchical clustering), a neural network (e.g., a multilayer perceptron (MLP), ResNet50, ResNet101, ResNet 152, VGG, DenseNet, PointNet, a multi-task model that predicts multiple ones of risk classification, biochemical status(es), and/ or medical condition(s), a multi-input model that receives epigenetic data associated with multiple biological sample types and/or assay types).

The ML model 318 may determine, based at least in part on the subset 316(p) and a set of parameters (e.g., a weight, bias, y term, split points, and/or φ term associated with a node and/or layer of the ML model 318) associated with the ML model 318, an estimate 320(p) of the target for which the ML model 318 is being trained (e.g., the epigenetic value associated with a DNA locus). The estimate 320(p) may be provided to a loss function 322, which may determine an error 324 based at least in part on a difference between the estimate 320(p) and ground truth data associated with the subset of epigenetic data 316(p). For example, the estimate 320(p) may comprise an estimated epigenetic value associated with a target DNA locus and/or a confidence score associated with the estimated epigenetic value, the subset of epigenetic data 316(p) may comprise epigenetic values associated with DNA loci other than the target DNA locus, and the ground truth may comprise a measured epigenetic value associated with the target DNA locus.

The loss function 322 may determine a parameter adjustment 326 to modify one or more parameters associated with the ML model 318 to minimize the error 324, such as according to a gradient descent technique, recursive partitioning, and/or the like. The type of loss function 322, error 324, and parameter adjustment 326 may depend on the type of ML model 318. For example, in an example where the ML model 318 comprises a neural network, the loss function 322 may modify the parameter(s) based at least in part on an error backpropagation technique such as, for example, a regression, gradient descent, and/or other iterative loss and determining the loss may comprise determining a crossentropy, Huber loss, mean absolute error ("L1 loss"), mean squared error ("L2 loss"), and/or the like. In an example where the ML model 318 comprises a decision tree, the loss function 322 may comprise a cost function that determines a cost associated with a first set of split points, a minimum number of training puts per leaf, depth, number of trees, and/or ensemble selection weights and tuning the ML model 318 may comprise adjusting the split points, a minimum number of training puts per leaf, depth, etc. (e.g., according to recursive partitioning) to minimize the cost. Tuning the parameter(s) to reduce the error 324 may increase an accuracy and/or recall of the ML model 318 in determining the estimated epigenetic value associated with the target DNA locus and/or the confidence associated therewith.

FIG. 4 illustrates a graph of mean absolute error rates associated with different feature selection algorithms (depicted on the left axis) for different machine-learning models (depicted on the x-axis) and different distribution patterns (depicted on the right y-axis) across 300 distinct target DNA loci (values summarized with box plots). More or less target DNA loci may be evaluated in additional or alternate examples. FIG. 5 illustrates a graph of spearman rank correlation coefficients associated with different feature selection algorithms (depicted on the left y-axis) for different machine-learning models (depicted on the x-axis) and different distribution patterns (depicted on the right y-axis) across 300 distinct target probes (values summarized with box plots). Both graphs demonstrate that it is feasible to use many different feature selection techniques and ML models to reproduce a wide variety of target probes to a high degree of accuracy. In some examples, multiple ML models may be combinatorially trained to output an estimated epigenetic value for a same target DNA locus, but using different types of ML models, different hyperparameters between ML models, and/or based on input measured epigenetic values associated with a same or different subset of DNA loci. The subset of DNA loci for which an ML model is trained may be based at least in part on the feature selection algorithm used to determine the subset (e.g., at operation 308) and as shown on the left y-axis of FIGS. 4 and 5. The subset may be additionally or alternatively determined based at least in part on a location of the target DNA locus within the DNA (e.g., relative to one or more other DNA loci), a distribution pattern associated with the DNA locus (e.g., bimodal, unimodal/univariate, low variance, high variance), a correlation of another DNA locus with the target DNA locus (e.g., a Spearman correlation), and/or the like.

In some examples, the techniques may additionally or alternatively comprise selecting an ML model from among the multiple ML models trained to output an estimated epigenetic value associated with the target DNA locus. The selection may be based at least in part on an accuracy and/or recall associated with the ML model (e.g., the accuracy and/or recall may meet or exceed a threshold, the accuracy and/or recall may be a highest accuracy and/or recall among the multiple ML models) and/or based at least in part on the subset of DNA loci upon which the ML model is trained. For example, the selection may balance the accuracy and/or recall against the probes that would be required to estimate the epigenetic value (e.g., the selection may be based at least in part on a preference to use less probes, such as a 27k array may provide).

In additional or alternate examples, one or more ML models may be selected in association with different array types. For example, a first ML model associated with a first subset of DNA loci associated with a 27k array and having satisfactory accuracy and/or recall (e.g., by being a maximum accuracy and/or recall among 27k array-trained ML models, having an accuracy and/or threshold that meets or exceeds a threshold), a second ML model associated with a second subset of DNA loci associated with a 450k array and having a satisfactory accuracy and/or recall, and/or the like.

Example System

Figure 6:
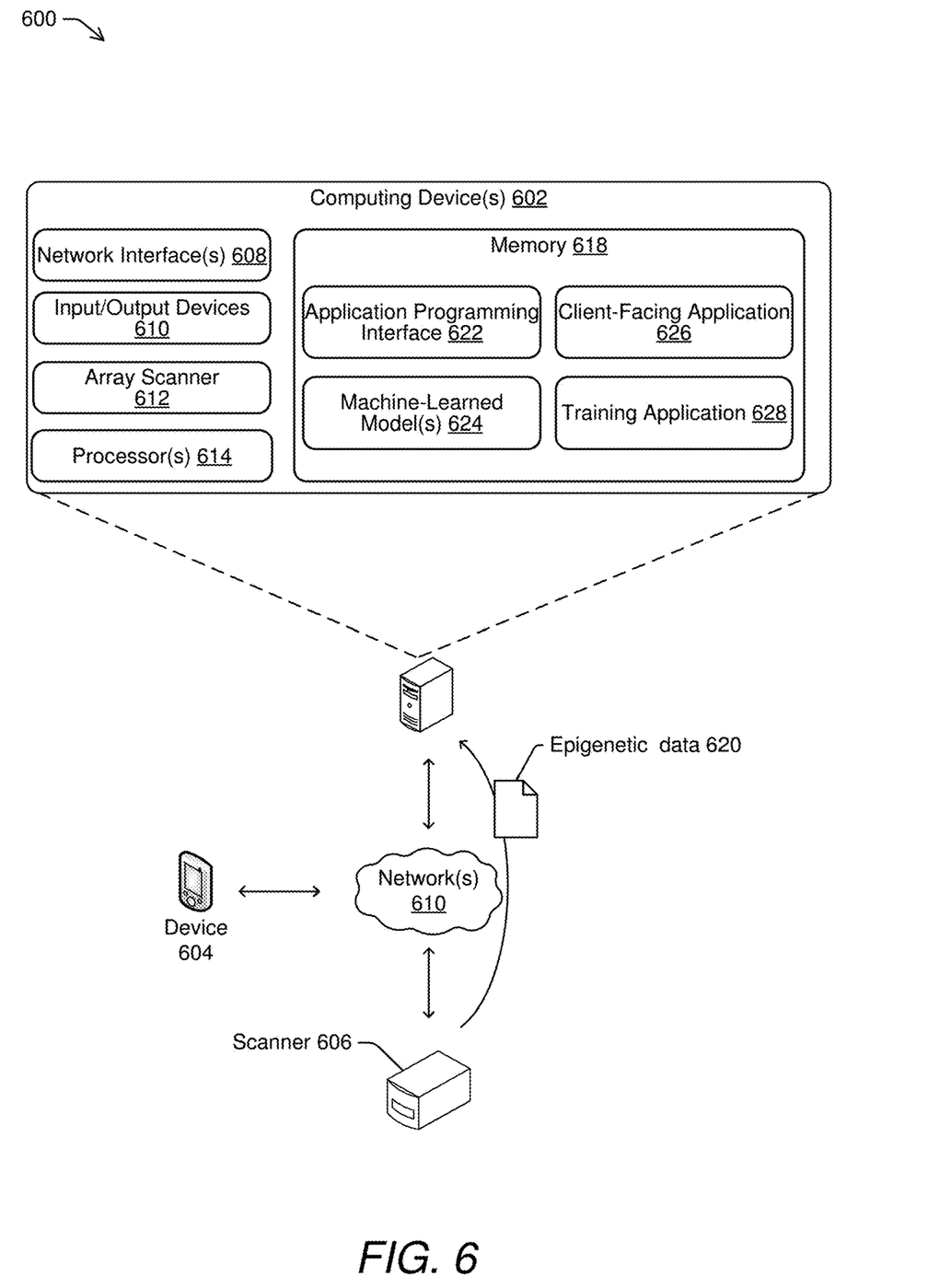
FIG. 6 illustrates a block diagram of an example architecture that implements the techniques discussed herein.

FIG. 6 depicts a block diagram of an example system 600 that implements the techniques discussed herein. In some instances, the system 600 may include service computing device(s) 602; a device 604; and a scanner 606. In some examples, service computing device(s) 602 may comprise one or more nodes of a distributed computing system (e.g., a cloud computing architecture).

In some examples, the service computing device(s) 602 may comprise network interface(s) 608, input/output device(s) 610, an array scanner 612 (or other type of apparatus for determining epigenetic data from a DNA sample), processor(s) 614, a display 616, and/or a memory 618.

Network interface(s) 608 may enable communication between the service computing device(s) 602 and one or more other local or remote computing device(s). For instance, the network interface(s) 608 may facilitate communication with other local computing device(s) of the service computing device(s). The network interface(s) 608 may additionally or alternatively enable the service computing device(s) 602 to communicate with a device 604 and/or scanner 606 via network(s) 610.

The network interface(s) 608 may include physical and/or logical interfaces for connecting the service computing device(s) 602 to another computing device or a network, such as network(s) 610. For example, the network interface(s) 602 may enable Wi-Fi-based communication such as via frequencies defined by the IEEE 802.11 standards, short range wireless frequencies such as Bluetooth®, cellular communication (e.g., 2G, 3G, 4G, 4G LTE, 5G, etc.) or any suitable wired or wireless communications protocol that enables the respective computing device to interface with the other computing device(s). In some instances, the service computing device(s) 602 may transmit instructions via the network interface(s) 608 to an application running on the device 604 to cause operations at the device 604 as discussed herein and/or transmit instructions to the scanner 606 to cause the specialized apparatus to determine epigenetic data 620 and/or transmit epigenetic data 620 to the service computing device(s) 602.

In some instances, the service computing device(s) 602 may include input/output device(s) 610 for human and/or artificial intelligence (AI) interaction with the service computing device(s) 602 (e.g., an application programming interface between an AI component and the service computing device(s) 602, keyboard, mouse, display, biometric scanner, microphone, speaker, tactile response generator).

Additionally or alternatively, the service computing device(s) 602 may comprise an array scanner 612. The array scanner 612 may represent a device similar or identical to the scanner 606 and/or may be any other component for determining epigenetic data from a DNA sample. For example, the array scanner 612 may detect fluorescent, radioactive, or other labels indicative of epigenetic of a DNA locus probed by a microarray.

The service computing device(s) 602 may include one or more processors, processor(s) 614, and memory 618 communicatively coupled with the processor(s) 614. The processor(s) 614 may be any suitable processor capable of executing instructions to process data and perform operations as described herein. By way of example and not limitation, the processor(s) 614 may comprise one or more central processing units (CPUs), graphics processing units (GPUs), integrated circuits (e.g., application-specific integrated circuits (ASICs), etc.), gate arrays (e.g., field-programmable gate arrays (FPGAs), etc.), and/or any other device or portion of a device that processes electronic data to transform that electronic data into other electronic data that may be stored in registers and/or memory.

Memory 618 may be an example of non-transitory computer-readable media. The memory 618 may store an operating system and one or more software applications, instructions, programs, and/or data to implement the methods described herein and the functions attributed to the various systems. In various implementations, the memory may be implemented using any suitable memory technology, such as static random access memory (SRAM), synchronous dynamic RAM (SDRAM), nonvolatile/Flash-type memory, or any other type of memory capable of storing information. The architectures, systems, and individual elements described herein may include many other logical, programmatic, and physical components, of which those shown in the accompanying figures are merely examples that are related to the discussion herein.

In some instances, the memory 618 may store an application programming interface (API) 622, ML model(s) 624, client facing application 626, and/or training application 628. In some examples, the API 624 may allow the device 604 or any other device (e.g., a device associated with a physician, laboratory, insurance company, and/or the like) to transmit requests to the service computing device(s) 602, causing the service computing device(s) 602 to conduct any of the operations discussed herein, and/or to receive responses from the service computing device(s) 602, which may comprise output(s) of the machine-learned model(s) 602 and/or determinations made according to the techniques discussed herein. In some examples, the API 622 may make some of the determinations discussed herein, e.g., whether sufficient data is available to estimate a target metric, whether available data is sufficient to satisfy a target criterion, selecting ML model(s) to which to provide input data, and/or the like. In some examples, the API 622 may be based at least in part on the representational state transfer (REST) protocol, simple object access protocol (SOAP), and/or JavaScript. In some examples, the API 622 may allow computationally heavy or proprietary functions (e.g., such as the ML model(s), criteria, and/or hierarchies, and/or use thereof) to be stored remotely from users of the techniques described herein, while still providing data determined according to the techniques discussed herein to computing devices associated with the users.

For example, device 604 may execute a client-side application 632 that transmits requests to the API 622 and receives responses therefrom. In some examples, the responses may comprise the instructions discussed herein. In some examples, the client-side application may cause display of the UI discussed herein and may enable/disable selection of a coverage level and/or payment level, as discussed above.

ML model(s) 624 may include and/or represent any of the ML models discussed herein and may comprise software, hardware (e.g., a circuit configured according to parameters determined during training), or a combination thereof (e.g., an FPGA configured as an ML model). The criteria and/or hierarchies 628 may comprise a target criterion, an input criterion, and/or any of the hierarchies discussed herein (e.g., hierarchy of risk classifications, hierarchy of assays, hierarchy of biochemical states and/or medical conditions, relation between biochemical states and a medical condition). In some examples, the training application 628 may comprise software instructions for training the ML model(s) 624 (e.g., according to example process 300).

It should be noted that while FIG. 6 illustrates components of service computing device(s) 602 as being within a single system the components may alternatively be stored, executed, or exist at different systems that may be communicatively coupled. Moreover, although a component may be depicted as being part of service computing device(s) 602, alternatively, the component may be stored, executed, or exist at device 604, scanner 606, and/or any other device.

Example Clauses

A. A method comprising: receiving a set of epigenetic data associated with a subject; receiving an indication of a target DNA locus; determining, based at least in part on the target DNA locus, a subset of the set of epigenetic data; providing the subset to a first machine-learning (ML) model; and receiving, from the first ML model, an estimated epigenetic value associated with the target DNA locus.

B. The method of paragraph A, wherein the method further comprises selecting the first ML model, from among one or more ML models, based at least in part on at least one of the target DNA locus, a biological sample type associated with the epigenetic data, or an assay type by which the set of epigenetic data was determined.

C. The method of either paragraph A or B, wherein: the set of epigenetic data was determined based at least in part on a biological sample received from the subject; the biological sample comprises at least one of saliva or blood.

D. The method of any one of paragraphs A-C, wherein determining the subset is based at least in part on at least one of a distribution pattern associated with the target DNA locus, a location of the target DNA locus compared to one or more other DNA loci, a correlation between the target DNA locus and another DNA locus, or one or more DNA loci associated with the first ML model.

E. The method of any one of paragraphs A-D, wherein the subject is a first subject and the method further comprises training the first ML model, wherein training the first ML model comprises: receiving a plurality of training sets of epigenetic data associated with a plurality of DNA loci; determining, based at least in part on a feature reduction algorithm and the target DNA locus, a subset of DNA loci from among the plurality of DNA loci; and training the first ML model to output an estimated epigenetic value associated with the target DNA locus based at least in part on epigenetic values associated with the subset of DNA loci.

F. The method of any one of paragraphs A-E, wherein: receiving the set of epigenetic data is based at least in part on assaying a biological sample received from the subject, wherein assaying the biological sample comprises determining one or more signals associated with at least one of a sequencing protocol or probes of a microarray; and the method further comprises determining that the probe associated with the target DNA locus failed or is unavailable.

G. The method of any one of paragraphs A-F, wherein receiving the indication of the target DNA locus is based at least in part on determining that a probe associated with the target DNA locus failed, is inaccurate, or is unavailable, wherein: the probe was used to assay a biological sample associated with the subject to determine the set of epigenetic data; and determining that the probe failed or is inaccurate comprises: receiving a measured epigenetic value associated with the target DNA locus, determining a difference between the estimated epigenetic value and the measured epigenetic value, and determining that the difference meets or exceeds a threshold difference.

H The method of any one of paragraphs A-G, further comprising determining, based at least in part on the estimated epigenetic value, at least one of a biochemical state associated with the subject or a medical status associated with the subject.

I. A system comprising: one or more processors; and a memory storing processor-executable instructions that, when executed by the one or more processors, cause the system to perform operations comprising: receiving a set of epigenetic data associated with a subject; receiving an indication of a target DNA locus; determining, based at least in part on the target DNA locus, a subset of the set of epigenetic data; providing the subset to a first machine-learning (ML) model; and receiving, from the first ML model, an estimated epigenetic value associated with the target DNA locus.

J. The system of paragraph I, wherein the operations further comprise selecting the first ML model, from among one or more ML models, based at least in part on at least one of the target DNA locus, a biological sample type associated with the epigenetic data, or an assay type by which the set of epigenetic data was determined.

K. The system of either paragraph I or J, wherein determining the subset is based at least in part on at least one of a distribution pattern associated with the target DNA locus, a location of the target DNA locus compared to one or more other DNA loci, a correlation between the target DNA locus and another DNA locus, or one or more DNA loci associated with the first ML model.

L. The system of any one of paragraphs I-K, wherein receiving the indication of the target DNA locus is based at least in part on determining that a probe associated with the target DNA locus failed, is inaccurate, or is unavailable, wherein: the probe was used to assay a biological sample associated with the subject to determine the set of epigenetic data; and determining that the probe failed or is inaccurate comprises: receiving a measured epigenetic value associated with the target DNA locus, determining a difference between the estimated epigenetic value and the measured epigenetic value, and determining that the difference meets or exceeds a threshold difference.

M. The system of any one of paragraphs I-L, wherein the operations further comprise determining, based at least in part on the estimated epigenetic value, at least one of a biochemical state associated with the subject or a medical status associated with the subject.

N. The system of any one of paragraphs I-M, wherein the subject is a first subject and the operations further comprise training the first ML model, wherein training the first ML model comprises: receiving a plurality of training sets of epigenetic data associated with a plurality of DNA loci; determining, based at least in part on a feature reduction algorithm and the target DNA locus, a subset of DNA loci from among the plurality of DNA loci; and training the first ML model to output an estimated epigenetic value associated with the target DNA locus based at least in part on epigenetic values associated with the subset of DNA loci.

O. A non-transitory computer-readable medium storing computer-executable instructions that, when executed by one or more processors, cause the one or more processors to perform operations comprising: receiving a set of epigenetic data associated with a subject; receiving an indication of a target DNA locus; determining, based at least in part on the target DNA locus, a subset of the set of epigenetic data;

providing the subset to a first machine-learning (ML) model; and receiving, from the first ML model, an estimated epigenetic value associated with the target DNA locus.

P. The non-transitory computer-readable medium of paragraph O, wherein the operations further comprise selecting the first ML model, from among one or more ML models, based at least in part on at least one of the target DNA locus, a biological sample type associated with the epigenetic data, or an assay type by which the set of epigenetic data was determined.

Q. The non-transitory computer-readable medium of either paragraph O or P, wherein determining the subset is based at least in part on one or more DNA loci associated with the first ML model.

R. The non-transitory computer-readable medium of any one of paragraphs O-Q, wherein receiving the indication of the target DNA locus is based at least in part on determining that a probe associated with the target DNA locus failed, is inaccurate, or is unavailable, wherein: the probe was used to assay a biological sample associated with the subject to determine the set of epigenetic data; and determining that the probe failed or is inaccurate comprises: receiving a measured epigenetic value associated with the target DNA locus, determining a difference between the estimated epigenetic value and the measured epigenetic value, and determining that the difference meets or exceeds a threshold difference.

S. The non-transitory computer-readable medium of any one of paragraphs O-R, wherein the operations further comprise determining, based at least in part on the estimated epigenetic value, at least one of a biochemical state associated with the subject or a medical status associated with the subject.

T. The non-transitory computer-readable medium of any one of paragraphs O-S, wherein: receiving the set of epigenetic data is based at least in part on assaying a biological sample received from the subject, wherein assaying the biological sample comprises determining one or more signals associated with at least one of a sequencing protocol or probes of a microarray; and the method further comprises determining that the probe associated with the target DNA locus failed or is unavailable.

U. The method, system, or non-transitory computer-readable medium of any one of claims B, K, or P, wherein the assay type comprises at least one of: bisulfite sequencing; pyrosequencing; epigenetic-sensitive single-strand conformation analysis (MS-SSCA); high resolution melting analysis (HRM); epigenetic-sensitive single nucleotide primer extension (MS-SnuPE); base-specific cleavage/MALDI-TOF; epigenetic-specific PCR (MSP); one or more microarrays; or msp I cleavage.

V. The method of paragraph F, wherein selecting the subset of the multiple DNA loci is further based at least in part on: classifying the first locus as at least one of univariately-related to the target DNA locus, bimodally-related to the target DNA locus, or trimodally-related to the target DNA locus, based at least in part on the target epigenetic data and the plurality of training sets of epigenetic data; and selecting the subset based at least in part on the classifying.

W. The method of any one of paragraphs F-V, wherein determining the subset of epigenetic data is based at least in part on determining that the subset of epigenetic data comprise epigenetic values associated with the subset of the other DNA loci.

While the example clauses described above are described with respect to one particular implementation, it should be understood that, in the context of this document, the content of the example clauses can also be implemented via a method, device, system, computer-readable medium, and/or another implementation. Additionally, any of examples A-AN may be implemented alone or in combination with any other one or more of the examples A-AN.

CONCLUSION

Although the subject matter has been described in language specific to structural features and/or methodological acts, it is to be understood that the subject matter defined in the appended claims is not necessarily limited to the specific features or acts described. Rather, the specific features and acts are disclosed as example forms of implementing the claims.

The components described herein represent instructions that may be stored in any type of computer-readable medium and may be implemented in software and/or hardware. All of the methods and processes described above may be embodied in, and fully automated via, software code components and/or computer-executable instructions executed by one or more computers or processors, hardware, or some combination thereof. Some or all of the methods may alternatively be embodied in specialized computer hardware.

Conditional language such as, among others, "may," "could," "may" or "might," unless specifically stated otherwise, are understood within the context to present that certain examples include, while other examples do not include, certain features, elements and/or steps. Thus, such conditional language is not generally intended to imply that certain features, elements and/or steps are in any way required for one or more examples or that one or more examples necessarily include logic for deciding, with or without user input or prompting, whether certain features, elements and/or steps are included or are to be performed in any particular example.

Conjunctive language such as the phrase "at least one of X, Y or Z," unless specifically stated otherwise, is to be understood to present that an item, term, etc. may be either X, Y, or Z, or any combination thereof, including multiples of each element. Unless explicitly described as singular, "a" means singular and plural.

Any routine descriptions, elements or blocks in the flow diagrams described herein and/or depicted in the attached figures should be understood as potentially representing modules, segments, or portions of code that include one or more computer-executable instructions for implementing specific logical functions or elements in the routine. Alternate implementations are included within the scope of the examples described herein in which elements or functions may be deleted, or executed out of order from that shown or discussed, including substantially synchronously, in reverse order, with additional operations, or omitting operations, depending on the functionality involved as would be understood by those skilled in the art.

In the description of examples, reference is made to the accompanying drawings that form a part hereof, which show by way of illustration specific examples of the claimed subject matter. It is to be understood that other examples can be used and that changes or alterations, such as structural changes, can be made. Such examples, changes or alterations are not necessarily departures from the scope with respect to the intended claimed subject matter. While the steps herein can be presented in a certain order, in some cases the ordering can be changed so that certain inputs are provided at different times or in a different order without changing the function of the systems and methods described.

The disclosed procedures could also be executed in different orders. Additionally, various computations that are herein need not be performed in the order disclosed, and other examples using alternative orderings of the computations could be readily implemented. In addition to being reordered, the computations could also be decomposed into sub-computations with the same results.

What is claimed is:

1. A method comprising:
   training a first machine-learning (ML) model to estimate an epigenetic value associated with a subject, wherein the training comprises altering one or more parameters of the first ML model based at least in part on a difference between an output of the first ML model and a ground truth epigenetic value to obtain a trained first ML model;
   receiving a set of epigenetic data associated with a subject, wherein the set of epigenetic data is determined by an assay configured with a plurality of probes to determine an epigenetic status at each locus of a set of deoxyribonucleic acid (DNA) loci of a biological sample;
   receiving an indication of a target DNA locus associated with the biological sample;
   determining that a probe associated with the target DNA locus failed or that at least one of the probe or the target DNA locus is unavailable on the assay;
   determining, based at least in part on the target DNA locus and determining that the probe failed or is unavailable, a subset of the set of epigenetic data; and
   determining, by the trained first ML model and based at least in part on the subset of epigenetic data, an estimated epigenetic value associated with the target DNA locus, wherein the estimated epigenetic value comprises an estimated probe intensity, an estimated probe intensity ratio, an estimated beta-value, or an estimated M-value associated with the target DNA locus.

2. The method of claim 1, wherein the method further comprises selecting the trained first ML model, from among one or more trained ML models, based at least in part on at least one of the target DNA locus, a biological sample type associated with the set of epigenetic data, or an assay type by which the set of epigenetic data was determined.

3. The method of claim 1, wherein:
   the set of epigenetic data was determined based at least in part on the biological sample received from the subject; and
   the biological sample comprises at least one of saliva or blood.

4. The method of claim 1, wherein determining the subset is based at least in part on at least one of a distribution pattern associated with the target DNA locus, a location of the target DNA locus compared to one or more other DNA loci, a correlation between the target DNA locus and another DNA locus, or one or more DNA loci associated with the trained first ML model.

5. The method of claim 1, wherein:
   the subject is a first subject;
   training the first ML model comprises:
      receiving a plurality of training sets of epigenetic data associated with a plurality of DNA loci; and
      determining, based at least in part on a feature reduction algorithm and the target DNA locus, a subset of DNA loci from among the plurality of DNA loci; and
   altering the one or more parameters of the first ML model based at least in part on the difference comprises determining a loss based at least in part on the difference and altering the one or more parameters is estimated to reduce the loss.

6. The method of claim 1, wherein receiving the set of epigenetic data is based at least in part on assaying the biological sample received from the subject, wherein assaying the biological sample comprises determining one or more signals associated with at least one of a sequencing protocol or probes of a microarray.

7. The method of claim 1, wherein: determining that the probe failed comprises:
   receiving a measured epigenetic value associated with the target DNA locus,
   determining a difference between the estimated epigenetic value and the measured epigenetic value, and
   determining that the difference meets or exceeds a threshold difference.

8. The method of claim 1, further comprising determining, based at least in part on the estimated epigenetic value, at least one of a biochemical state associated with the subject or a medical status associated with the subject.

9. A system comprising:
   one or more processors; and
   a memory storing processor-executable instructions that, when executed by the one or more processors, cause the system to perform operations comprising:
      training a first machine-learning (ML) model to estimate an epigenetic value associated with a subset of epigenetic data, wherein training includes a plurality of epigenetic data associated with biological samples received from a plurality of subjects, the training comprising iteratively;
         providing a first subset of the plurality of epigenetic data to the first ML model;
         receiving, from the first ML model, an output indicating an epigenetic value; and
         altering one or more parameters of the first ML model based at least in part on a difference between the output and a ground truth epigenetic value associated with the subset of epigenetic data to obtain a trained first ML model;
      receiving a set of epigenetic data associated with a subject;
      receiving an indication of a target deoxyribonucleic acid (DNA) locus;
      determining that a probe associated with the target DNA locus failed or that at least one of the probe or the target DNA locus is unavailable on an assay that determined the set of epigenetic data;
      determining, based at least in part on the target DNA locus, a second subset of the set of epigenetic data, wherein the second subset is determined based at least in part on a feature reduction algorithm that is based at least in part on the set of epigenetic data and the target DNA locus;
      providing, to one or more input nodes of the trained first ML model, the second subset;
      determining, by one or more hidden layers of the trained first ML model based at least in part on an output of the input nodes, an intermediate output; and
      determining, by an output layer of the trained first ML model based at least in part on the intermediate output, an estimated epigenetic value quantifying a property associated with the target DNA locus.

10. The system of claim 9, wherein the operations further comprise selecting the trained first ML model, from among one or more trained ML models, based at least in part on at least one of the target DNA locus, a biological sample type associated with the epigenetic data, or an assay type by which the set of epigenetic data was determined.

11. The system of claim 9, wherein determining the second subset is based at least in part on at least one of a distribution pattern associated with the target DNA locus, a location of the target DNA locus compared to one or more other DNA loci, a correlation between the target DNA locus and another DNA locus, or one or more DNA loci associated with the trained first ML model.

12. The system of claim 9, wherein determining that the probe associated with the target DNA locus failed comprises:
  receiving a measured epigenetic value associated with the target DNA locus,
  determining a difference between the estimated epigenetic value and the measured epigenetic value, and
  determining that the difference meets or exceeds a threshold difference.

13. The system of claim 9, wherein the operations further comprise determining, based at least in part on the estimated epigenetic value, at least one of a biochemical state associated with the subject or a medical status associated with the subject.

14. A non-transitory computer-readable medium storing computer-executable instructions that, when executed by one or more processors, cause the one or more processors to perform operations comprising:
  training a first machine-learning (ML) model to estimate an epigenetic value associated with a subject, wherein the training comprises altering one or more parameters of the first ML model based at least in part on a difference between an output of the first ML model and a ground truth epigenetic value to obtain a trained first ML model;
  receiving a set of epigenetic data associated with a subject;
  receiving an indication of a target deoxyribonucleic acid (DNA) locus;
  determining that a probe associated with the target DNA locus failed or that at least one of the probe or the target DNA locus is unavailable on an assay that determined the set of epigenetic data;
  determining, based at least in part on the target DNA locus, a subset of the set of epigenetic data, wherein the subset is determined based at least in part on a feature reduction algorithm that is based at least in part on the set of epigenetic data and the target DNA locus;
  providing, to one or more input nodes of the trained first ML model, the subset;
  determining, by one or more hidden layers of the trained first ML model based at least in part on an output of the input nodes, an intermediate output; and
  determining, by an output layer of the trained first ML model based at least in part on the intermediate output, an estimated epigenetic value quantifying a property associated with the target DNA locus and a confidence score indicating an accuracy of the estimated epigenetic value.

15. The non-transitory computer-readable medium of claim 14, wherein a methylation array is an array that assays an epigenetic level at over 27,500 DNA locations.

16. The non-transitory computer-readable medium of claim 14, wherein the operations further comprise selecting the trained first ML model, from among one or more trained ML models, based at least in part on at least one of the target DNA locus, a biological sample type associated with the epigenetic data, or an assay type by which the set of epigenetic data was determined.

17. The non-transitory computer-readable medium of claim 14, wherein determining the subset is based at least in part on one or more DNA loci associated with the trained first ML model.

18. The non-transitory computer-readable medium of claim 14, wherein receiving the indication of the target DNA locus is based at least in part on determining that a probe associated with the target DNA locus failed, is inaccurate, or is unavailable, wherein:
  the probe was used to assay a biological sample associated with the subject to determine the set of epigenetic data; and
  determining that the probe failed or is inaccurate comprises:
    receiving a measured epigenetic value associated with the target DNA locus,
    determining a difference between the estimated epigenetic value and the measured epigenetic value, and
    determining that the difference meets or exceeds a threshold difference.

19. The non-transitory computer-readable medium of claim 14, wherein the operations further comprise determining, based at least in part on the estimated epigenetic value, at least one of a biochemical state associated with the subject or a medical status associated with the subject.

20. The non-transitory computer-readable medium of claim 14, wherein receiving the set of epigenetic data is based at least in part on assaying a biological sample received from the subject, wherein assaying the biological sample comprises determining one or more signals associated with at least one of a sequencing protocol or probes of a microarray.

* * * * *